(12) United States Patent
Nakagawa et al.

(10) Patent No.: US 7,115,721 B2
(45) Date of Patent: Oct. 3, 2006

(54) MICROORGANISM, ITS PRODUCT AND UTILIZATION THEREOF

(75) Inventors: Akira Nakagawa, 1-33-47, Yotsuya, Fuchu-shi, Tokyo 183-0035 (JP); Senji Takahashi, Tokyo (JP); Toshitsugu Miyazaki, Kobe (JP); Yuuko Osanai, Saitama (JP); Kunio Kosaka, Tokyo (JP); Koji Nagai, Tokyo (JP); Nakako Arao, Tokyo (JP); Kouichi Tanaka, Tokyo (JP)

(73) Assignees: Astellas Pharma Inc., Tokyo (JP); Akira Nakagawa, Tokyo (JP); Nagase & Co., Ltd,, Osaka (JP)

( * ) Notice: Subject to any disclaimer, the term of this patent is extended or adjusted under 35 U.S.C. 154(b) by 34 days.

(21) Appl. No.: 10/502,949

(22) PCT Filed: Jan. 29, 2003

(86) PCT No.: PCT/JP03/00851

§ 371 (c)(1),
(2), (4) Date: Jul. 29, 2004

(87) PCT Pub. No.: WO03/064668

PCT Pub. Date: Aug. 7, 2003

(65) Prior Publication Data

US 2005/0063927 A1    Mar. 24, 2005

(30) Foreign Application Priority Data

Jan. 30, 2002 (JP) ............................ 2002-020981
Jan. 30, 2002 (JP) ............................ 2002-021224

(51) Int. Cl.
  *C07H 15/00* (2006.01)
  *C07H 17/00* (2006.01)
  *A61K 8/00* (2006.01)
  *A61Q 5/08* (2006.01)

(52) U.S. Cl. ..................... 536/17.9; 536/4.1; 536/17.2; 536/18.7; 514/25; 514/27; 424/62; 424/401

(58) Field of Classification Search ................. 536/4.1, 536/17.2, 17.9, 18.7; 514/25, 27; 424/62, 424/401
See application file for complete search history.

(56) References Cited

U.S. PATENT DOCUMENTS

2003/0198610 A1 * 10/2003 Nakayama et al. ........... 424/59

FOREIGN PATENT DOCUMENTS

CA  2027723  4/1991
EP  0404661  12/1990

* cited by examiner

*Primary Examiner*—Shaojia Anna Jiang
*Assistant Examiner*—Traviss McIntosh
(74) *Attorney, Agent, or Firm*—Finnegan, Henderson, Farabow, Garrett & Dunner, LLP (57) ABSTRACT

There are provided a novel microorganism *Enterobacter* sp. B20 strain which produces (E)-4-(2-isocyanovinyl)phenyl α-rhamnopyranoside having a favorable effect of inhibiting melanogenesis and α-L-rhamnopyranoside produced thereby. This novel microorganism is a gram-negative bacillus isolated from soil and shows motility owing to polar flagellum. The α-L-rhamnopyranoside, which is produced by culturing the microorganism under aerobic conditions at a culture temperature of 10 to 37° C. and at a medium pH of about 5 to 9 usually for about 1 to 7 days, is useful as a highly safe and stable whitening agent.

5 Claims, 3 Drawing Sheets

MICROORGANISM, ITS PRODUCT AND UTILIZATION THEREOF

TECHNICAL FIELD

The present invention relates to a novel microorganism capable of producing (E)-4-(2-isocyanovinyl)phenyl α-L-rhamnopyranoside, a novel compound having a melanogenesis inhibitory action based on a tyrosinase inhibitory activity and effective for preventing and diminishing pigmentation, spots, or freckles caused after exposure to sunlight; chloasma, and the like, to a novel compound produced by the microorganism having a melanogenesis inhibitory action based on a tyrosinase inhibitory activity and effective for preventing and diminishing pigmentation, spots, or freckles caused after exposure to sunlight; chloasma, and the like, and to an agent for external skin application, particularly a whitening agent containing this compound.

BACKGROUND ART

Pigmentation of skin includes various types such as spots and freckles, as well as pigmentation due to skin diseases such as chloasma. As a possible action mechanism of pigmentation, diffusion and deposition of pigment melanin produced in melanocytes, which are cells present in epidermic cells, due to exposure to sunlight, abnormalities in hormones, and the like can be given in general. Controlling production of enzyme tyrosinase which is the first step of melanogenesis in the melanocytes or directly inhibiting enzyme tyrosinase is important for retardation of melanin pigment production. Kojic acid and arbutin conventionally used are typical agents having this effect. Melanin is produced by enzymatic or nonenzymatic oxidation of dopa or dopa quinone which is produced by the action of enzyme tyrosinase. Inhibiting this reaction is also effective for controlling melanogenesis. Ascorbic acid, hydroquinone, and the like can be given as typical agents for this purpose.

However, these conventional agents do not necessarily exhibit a sufficient effect. Development of a whitening agent exhibiting an excellent melanogenesis inhibitory action and being highly safe as a raw material for a cosmetic composition or an agent for external skin application has been desired.

DISCLOSURE OF THE INVENTION

As a result of extensive studies into substances produced by a great number of microorganisms, the inventors of the present invention have discovered that a novel microorganism belonging to the genus *Enterobacter* produces a substance exhibiting excellent tyrosinase inhibitory activity and melanogenesis inhibitory action. The inventors have been successful in isolating a novel compound (E)-4-(2-isocyanovinyl)phenyl α-L-rhamnopyranoside (hereinafter referred to as compound (I)) from a culture broth of the microorganism. The inventors have further found that the compound (I) has an outstanding effect of preventing and diminishing pigmentation and that a highly safe whitening agent exhibiting an excellent whitening effect can be obtained by admixing this compound therein. These findings have led to the completion of the present invention.

Specifically, the present invention relates first to (E)-4-(2-isocyanovinyl)phenyl α-L-rhamnopyranoside or its salt having a melanogenesis inhibitory action and being useful as a whitening agent, second to an agent for external skin application, particularly a whitening agent, comprising this compound, and third to a novel microorganism *Enterobacter* sp. B20 strain capable of producing (E)-4-(2-isocyanovinyl) phenyl α-L-rhamnopyranoside.

BEST MODE FOR CARRYING OUT THE INVENTION

The present invention will now be described in detail.

The novel microorganism of the present invention belongs to the genus *Enterobacter* isolated from soil and has the following microbiological characteristics.

1) Morphological Characteristics

The strain is a gram-negative bacillus and shows motility using polar flagellum. The cells have a dimension of 0.8–1.1 μm×1.0–2.2 μm. Formation of spores is not observed.

2) Culture Characteristics

Light yellowish brown colonies are formed on a nutrient agar medium. The colonies are round and have a smooth surface. When cultured in a nutrient broth, the cells form a membrane on the surface of the medium and the whole culture medium becomes cloudy. In paracentesis culture using nutrient gelatin, no liquefaction of gelatin is observed. The cells are neither coagulated nor peptonized after incubation for one week in litmus milk.

3) Physiological Characteristics

Physiological characteristics (1) of B20 strain Physiological characteristics and the like of the strain are summarized in Table 1.

TABLE 1

| | |
|---|---|
| Nitrate reduction | Positive |
| Denitrification | Positive |
| MR test | Positive |
| VP test | Negative |
| Indole production | Negative |
| Hydrogen sulfide production | Negative |
| Starch hydrolysis | Negative |
| Citric acid utilization | Positive |
| Nitrate utilization | Negative |
| Ammonium salt utilization | Positive |
| Water-soluble fluorescent pigment production | Negative |
| Urease | Negative |
| Oxidase | Negative |
| Catalase | Positive |
| Growth temperature range | 10–37° C. |
| Optimum growth temperature | 20–32° C. |
| Growth pH range | pH 5–9 |
| Optimum growth pH | pH 5–8 |
| Growth under unaerobic conditions | Positive |
| OF test | Fermentation-type |
| Arginine decomposition reaction | Negative |
| Growth in 3% NaCl-added nutrient culture broth | Positive |

Physiological Characteristics (2) of B20 Strain

Acid production from various saccharides is summarized in Table 2.

TABLE 2

| Type of saccharide | Acid production |
|---|---|
| L-arabinose | Positive |
| D-xylose | Positive |
| D-glucose | Positive |
| D-mannose | Positive |
| D-fructose | Positive |
| Sucrose | Negative |
| Inositol | Negative |
| D-mannitol | Positive |
| D-galactose | Positive |
| Maltose | Positive |
| Trehalose | Positive |
| Lactose | Positive |
| D-sorbitol | Negative |
| Salicin | Positive |
| Glycerol | Positive |
| Starch | Negative |
| Cellobiose | Positive |

Physiological Characteristics (3) of B20 Strain

Assimilability of carbon sources is summarized in Table 3.

TABLE 3

| Type of carbon source | Assimilability |
|---|---|
| L-arabinose | Positive |
| D-xylose | Positive |
| D-glucose | Positive |
| D-mannose | Positive |
| D-fructose | Positive |
| Sucrose | Negative |
| Inositol | Negative |
| Rhamnose | Positive |
| Raffinose | Negative |
| D-mannitol | Positive |
| D-galactose | Positive |
| Maltose | Positive |
| Trehalose | Positive |
| Lactose | Positive |
| D-sorbitol | Positive |
| Salicin | Positive |
| Melibiose | Negative |
| Glycerol | Positive |
| Starch | Positive |
| Xanthin | Negative |
| Chitin | Negative |

Summarizing the above microbiological characteristics, the present strain is a gram-negative anaerobic bacillus and shows motility. The present strain grows at 10–37° C. and shows positive results in the nitrate reduction, denitrification, MR test, citric acid utilization, and catalase test. The present strain can produce acids from L-arabinose, D-xylose, D-glucose, D-mannose, D-fructose, D-mannitol, D-galactose, maltose, trehalose, lactose, salicin, glycerol, and cellobiose. The result of the OF test is a fermentation-type. On the other hand, the results of the VP test, indole production, hydrogen sulfide production, urease test, oxidase test, and arginine decomposition reaction are negative.

As a result of the identification based on the above characteristics with reference to Bergey's Manual of Systematic Bacteriology (1989) and other documents, this strain was judged to be a microorganism belonging to the genus *Enterobacter* and was named *Enterobacter* sp. B20 strain.

The strain was deposited with the International Patent Organism Depositary, National Institute of Advanced Science and Technology (Center No. 6, 1-1, Higashi 1-Chome, Tsukuba-shi, Ibaraki-ken, Japan) on Dec. 25, 2001 as FERM P-18666. The deposition was transferred to the deposition under the Budapest Treaty on Dec. 26, 2002 as FERM BP-8266. Since a microorganism easily mutates either artificially or naturally, it is needless to mention that the *Enterobacter* sp. B20 strain used in the present invention includes the microorganism separated from natural sources and mutants not only artificially mutated with ultraviolet radiation, X-rays, chemicals, or the like, but also naturally occurring.

Next, the method for producing the compound (I) of the present invention by culturing the *Enterobacter* sp. B20 strain will be explained.

Specifically, the compound (I) or its salt of the present invention can be obtained by culturing a microorganism belonging to the genus *Enterobacter* and capable of producing the compound (I) of the present invention, for example, the *Enterobacter* sp. B20 FERM P-18666 strain or its mutant strain. The culturing of the microorganism may be carried out based on the culturing method for general microorganisms.

The culture medium may be any medium containing nutrients utilized by a microorganism belonging to the genus *Enterobacter* and capable of producing the compound (I) of the present invention, for example, the *Enterobacter* sp. B20 strain. A synthetic medium, semisynthetic medium, and natural medium can be used. Any known nutrients may be added to the culture medium. As carbon sources used for the medium, L-arabinose, D-xylose, p-glucose, D-fructose, L-rhamnose, D-mannitol, mannose, lactose, D-galactose, maltose, trehalose, salicin, starch, glucose, dextrin, glycerol, vegetable oils, and the like can be given. As nitrogen sources, meat extract, peptone, gluten meal, cottonseed meal, soybean meal, peanut powder, fish meal, corn steep liquor, dry yeast, yeast extract, ammonium chloride, ammonium sulfate, ammonium nitrate, uric acid, and other organic and inorganic nitrogen sources can be given. Other metal salts such as a sulfate, nitrate, carbonate, and phosphate of sodium, potassium, magnesium, calcium, zinc, iron, cobalt, or the like can be optionally added. A growth promoting agent such as methionine, cysteine, cystine, thiosulfate, methyl oleate, lard oil and silicone oil; and a deforming agent such as a surfactant may also be added if necessary.

Culturing under aerobic conditions is generally advantageous. An incubation temperature in the range of 10–37° C. (refer to the above description on the physiological characteristics), and preferably about 20–32° C., can be used. In regard to the pH of the medium, good results can be obtained when the pH is controlled in the range of about 5–9, and preferably about 5–8. The culturing period is appropriately determined according to the medium composition and temperature conditions, usually in the range of about 1–7 days, and preferably about 2–5 days.

To isolate the objective substance of the present invention from the culture broth, conventional methods for extracting and purifying metabolites produced by microorganisms can be appropriately used. For example, the present substance in the culture broth is extracted with an organic solvent immiscible with water such as ethyl acetate from the culture broth as is or from the culture broth obtained by centrifuging the culture broth or by filtering the culture broth after the addition of a filter adjuvant. The present substance can also be obtained by causing the culture broth to come into contact with an appropriate carrier, thereby causing the carrier to adsorb the produced substance in the filtrate, and eluting the substance with an appropriate solvent. For example, a porous adsorptive resin such as Amberlite XAD-2, Diaion HP-20, Diaion CHP-20, or Diaion SP-900 is used to adsorb the present substance. Next, the adsorbed substance is eluted using a mixture of water and an organic solvent such as methanol, ethanol, acetone, butanol, or acetonitrile. In this instance, the mixing ratio of the organic solvent is increased gradually or continuously to obtain fractions containing the present substance. When an organic solvent such as ethyl acetate or chloroform is used for extraction, the solvent is added to the culture broth filtrate and the mixture is sufficiently shaken to extract the present substance. The fractions containing the present substance obtained using the above procedures can be further isolated and purified by conventional methods such as column chromatography using silica gel, ODS, or the like, centrifugal liquid-liquid partition chromatography, and high performance liquid chromatography (HPLC) using ODS. Specifically, the present substance can be isolated and purified by a means for manufacturing common physiologically active substances utilizing the difference in resolvability and solubility in a suitable solvent using a melanogenesis inhibitory activity as an index. These methods may be used either individually or in combination in any arbitrary order and may also be used repeatedly, depending upon the necessity.

The compound (I) of the present invention may form a salt with an acid. The acid includes an inorganic acid and organic acid. Specifically, acid addition salts with an inorganic acid such as hydrochloric acid, hydrobromic acid, hydroiodic acid, sulfuric acid, nitric acid, or phosphoric acid or with an organic acid such as formic acid, acetic acid, propionic acid, oxalic acid, malonic acid, succinic acid, fumaric acid, maleic acid, lactic acid, malic acid, tartaric acid, citric acid, methanesulfonic acid, or ethanesulfonic acid can be given. In addition, the compound (I) or its salt of the present invention includes all related substances such as a hydrate and various solvates, tautomers, and stereoisomers based on an asymmetrical carbon atom of the compound (I) or its salt. Moreover, the compound (I) or its salt of the present invention may have crystal polymorphs, which are all included in the present invention.

The agent for external skin application of the present invention can be prepared in any forms of cosmetic compositions, quasi-drugs, medical supplies, and the like according to conventional methods. A cream, milky lotion, face lotion, foundation, pack, lotion, gel, solution, and stick can be mentioned as specific examples.

The agent for external skin application of the present invention comprises the compound (I) or its salt of the present invention in an amount of preferably 0.00001–10 wt %, and particularly preferably 0.001–1 wt %. If less than 0.00001 wt %, the agent has only a poor skin whitening effect. On the other hand, an increase in the effect is not expected even if the compound (I) or the salt is added in an amount of more than 10 wt %.

In addition to the compound (I) or its salt of the present invention, various optional components used for common cosmetic compositions, quasi-drugs, medical supplies, and the like such as an oleum, humectant, thickener, antiseptic agent, emulsifying agent, pigment, powder, pH adjusting agent, medicinal ingredient, UV absorber, antioxidant, and perfume may be added to the agent for external skin application of the present invention, as appropriate.

EXAMPLES

Production of the compound (I) of the present invention will be specifically described by examples, which should not be construed as limiting the present invention.

Example 1

500 ml conical flasks were charged with 100 ml each of a medium (pH 7.0) containing glucose (10 g), potato starch (20 g), polypeptone (5 g), yeast extract (5 g), calcium carbonate (4 g), and distilled water (1 L), and the resultants were sterilized for 20 minutes at 120° C. An aliqout amount of *Enterobacter* sp. B20 strain cells well grown in a Bennett agar medium were scraped and inoculated, followed by shaking for three days at 28° C. and 220 rpm to obtain a seed culture solution. Next, 500 ml conical flasks were charged with 100 ml each of a medium (pH 5.5) containing glycerol (40 g), corn steep liquor (30 g), sodium nitrate (4 g), calcium carbonate (2 g), magnesium sulfate heptahydrate (0.2 g), and distilled water (1 L), and the resultants were sterilized for 20 minutes at 120° C. The above seed culture solution was inoculated into the broth in 200 flasks in an amount of 3 ml per flask and cultured for five days while shaking at 28° C. and 220 rpm.

20 L of thus obtained culture broth was centrifuged using a Sharples-type centrifugal machine to separate the cells from the supernatant culture solution. After adjusting to pH 7, the culture supernatant was extracted with 10 L of ethyl acetate. On the other hand, 20 L of water containing 80% acetone was added to the cells and the mixture was stirred for three hours. Diatomaceous earth was added to the mixture, followed by filtration by suction. The resulting acetone solution was concentrated by vacuum evaporation to remove acetone. The concentrate was extracted with ethyl acetate and the extract was concentrated to dryness. The ethyl acetate extract (8.4 g) obtained from the cells and supernatant solution was subjected to silica gel column chromatography (Silica gel 60, 70–230 mesh ASTM, Merck) and eluted sequentially using chloroform-methanol mixtures (100:1, 20:1, 10:1). The active fractions containing a melanogenesis inhibitor were concentrated to dryness to obtain a crude substance (1.2 g). The powder was applied to pass an Oasis HLB solid phase extraction cartridge (6 g/35 cc) and washed with distilled water (70 ml) and 50% methanol (70 ml). The active substance was eluted with 100% methanol (70 ml) and the eluant was concentrated to dryness to obtain active powder (517 mg). The powder was submitted to HPLC (Sensyu Pack Pegasil ODS; 20 i.d. ×250 mm) and eluted with a mixture of acetonitrile and water (30:70) to collect peaks exhibiting the activity. The collected fractions were concentrated to dryness to obtain (E)-4-(2-isocyanovinyl)phenyl α-L-rhamnopyranoside of the following formula (1) as white powder (110 mg).

Specifically, the compound (I) of the present invention is a glycoside of the following formula (1).

Physicochemical characteristics of the compound (I) of the above formula (1) are as follows.

Figure 1:
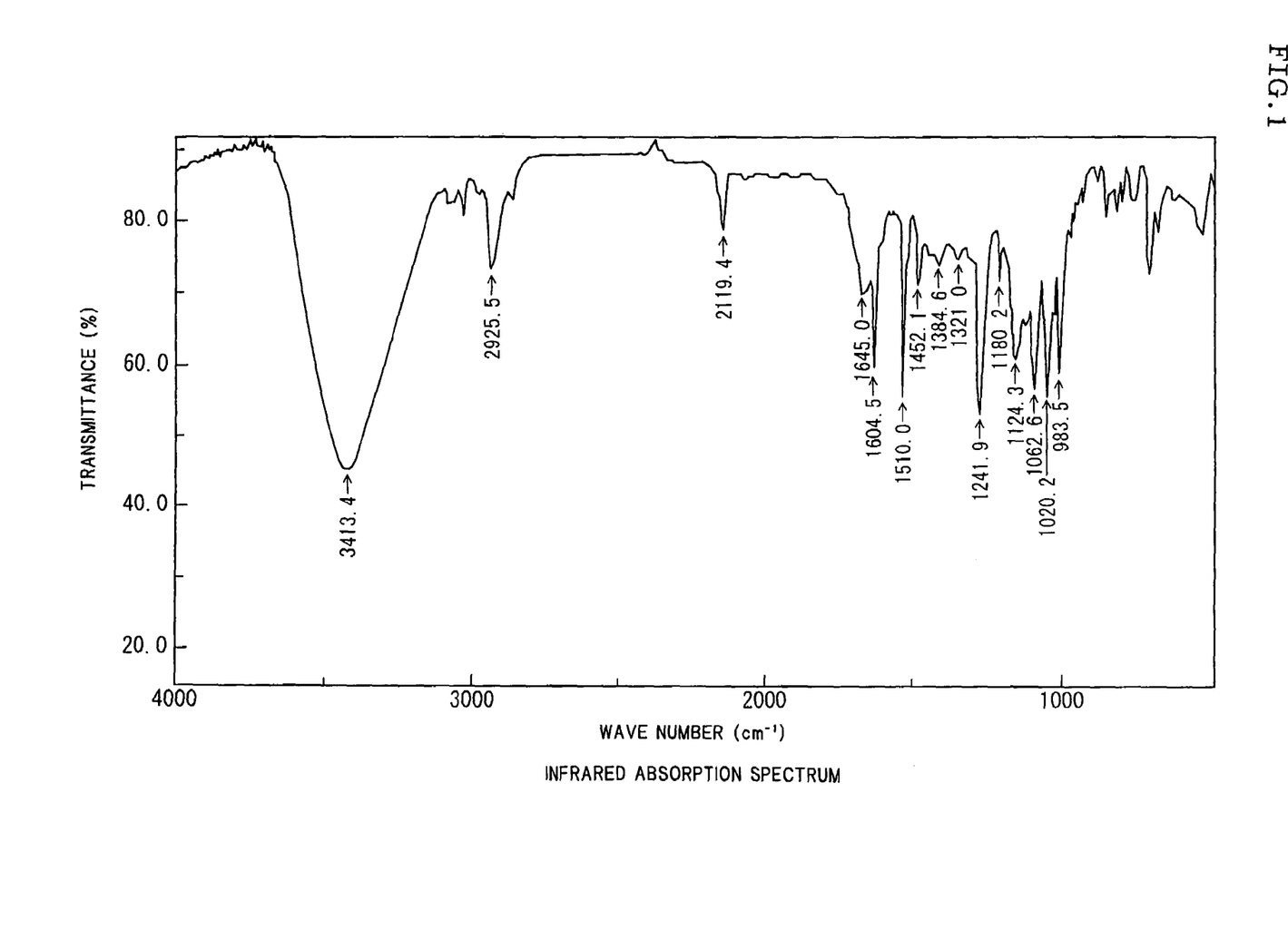
FIG. 1 shows an infrared absorption spectrum ($v_{max}$ (KBr) $cm^{-1}$) of the compound of the present invention.
Figure 2:
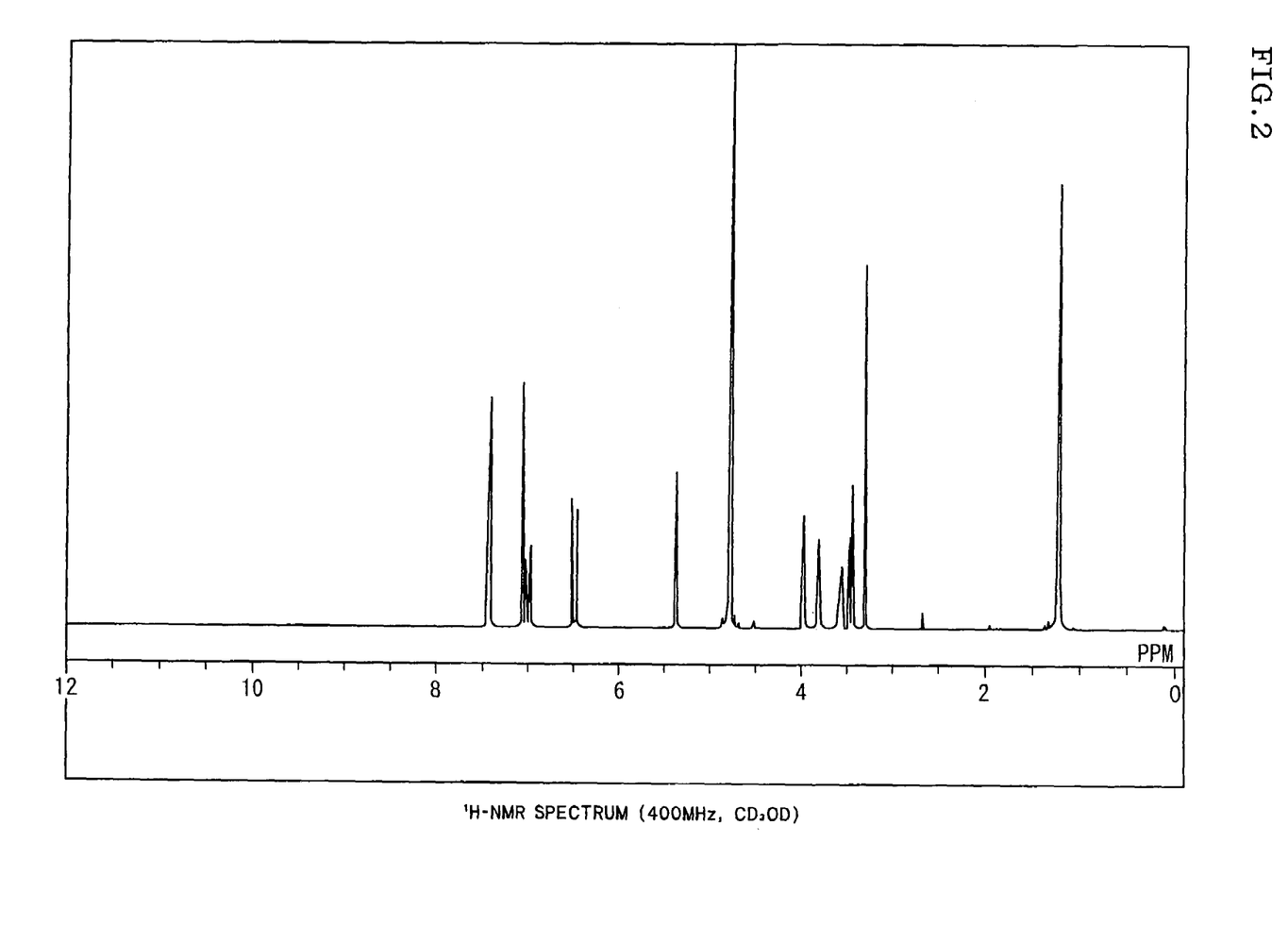
FIG. 2 shows an $^1$H-NMR spectrum of the compound of the present invention.
Figure 3:
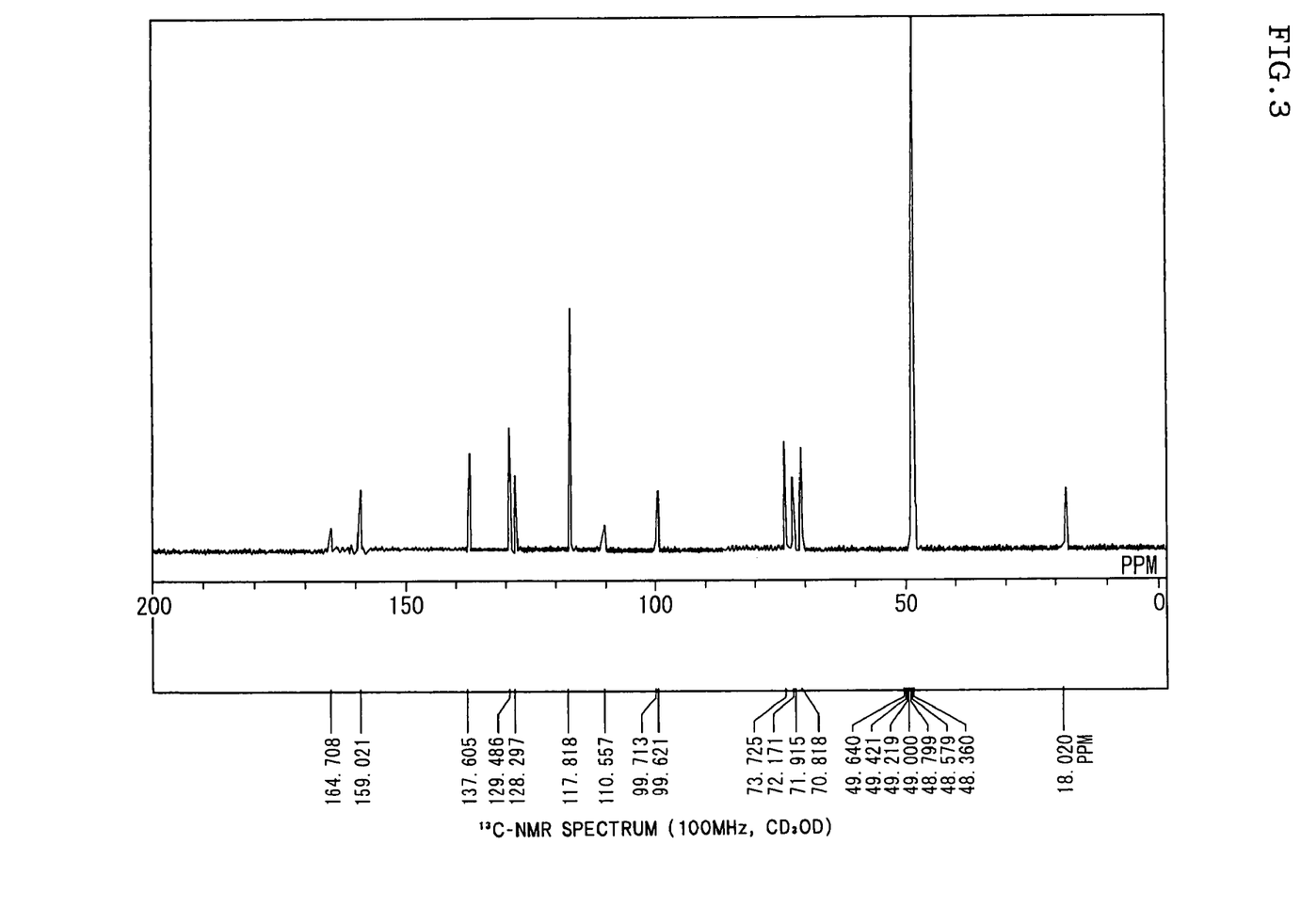
FIG. 3 shows a $^{13}$C-NMR spectrum of the compound of the present invention.

Color and form: white powder
Optical rotation: $[\alpha]_{25}^D$ -142° (c 0.1, methanol)
Molecular formula: $C_{15}H_{17}O_5N$
High resolution FAB mass spectrum:
Found: 292.1187 $(M+H)^-$.
Calculated: 292.1185 $(M+H)^+$.
Ultraviolet visible absorption spectrum ($\lambda_{max}^{MeOH}$ nm ($\epsilon$)):
210 (15,000), 221 (15,000), 281 (26,000)
Infrared absorption spectrum ($\gamma_{max}$ (KBr) $cm^{-1}$):
See FIG. 1.
$^1$H-NMR spectrum (400 MHz, $CD_3OD$): See FIG. 2.
$^{13}$C-NMR spectrum (100 MHz, $CD_3OD$): See FIG. 3.

Example 2

The inhibitory activity to tyrosinase originating from mushroom, inhibitory activity to tyrosinase originating from B16 melanoma, and inhibitory effect on melanogenesis of B16 melanoma of the compound (I) of the present invention were determined by the following methods.

Inhibitory Activity to Tyrosinase Originating from Mushroom

Tyrosinase originating from mushroom (Sigma company) was dissolved in a 0.05 M phosphate buffer (pH 6.8) to a concentration of 20 U/ml. L-dopa was adjusted to a concentration of 0.3 mg/ml with a 0.05 M phosphate buffer (pH 6.8). A 96-well plate was charged with 30 μl of the L-dopa solution and 30 μl of solutions of the compound (I) of the present invention at various concentrations, immediately followed by mixing with 30 μl of the tyrosinase solution originating from mushroom. After incubation at 25° C. for 10 minutes, the absorbance at 450 nm was measured using a microplate reader.

Inhibitory Activity to Tyrosinase Originating from B16 Melanoma

About $2.0\times10^5$/ampoule B16 melanoma cell strain preserved in a frozen state in liquid nitrogen was dissolved in a water bath at 37° C. and immediately suspended in 10 ml of a culture medium. After centrifugation at 800 rpm for five minutes, the supernatant liquid was discarded and the cells were suspended in 10 ml of a fresh culture medium. The suspension was again centrifuged under the same conditions, the supernatant liquid was discarded, and the cells were again suspended in a fresh culture medium.

About $4.0\times10^5$ cells were seeded in a 75 $cm^2$ flask. The cells were cultured at 37° C. in a 5% $CO_2$ atmosphere for one week while replacing the medium every 2–3 days. The culture medium in which the cells have grown to bring the medium into a subconfluent state was discarded. The surface of the cultured cells was washed with PBS(−), following which the cells were stripped using 0.25% trypsin. A medium containing serum was added to terminate the trypsin reaction. After loosening the cells by pipetting, the cell suspension was transferred to a centrifugal tube. After centrifugation at 800 rpm for five minutes, the supernatant liquid was discarded and the cells were suspended in a fresh culture medium. The number of cells was counted using a cytometer.

The $5\times10^5$ cells were seeded in a 175 $cm^2$ flask and incubated at 37° C. in a 5% $CO_2$ atmosphere for five days. The culture medium in a confluent state was discarded. The cell surface was washed with PBS(−), the cells were stripped using 0.25% trypsin, and a medium containing serum was added to terminate the trypsin reaction. The cells were loosened by pipetting. The cell suspension was collected in a 50 ml conical tube and centrifuged at 800 rpm for five minutes. The supernatant liquid was discarded and the cells were suspended in PBS(−) to wash the cells again in the PBS(−). The cells were re-suspended in a 0.05 M phosphate buffer (pH 6.8) and crushed in ice using a homogenizer. Sample tubes of 1.5 ml were charged with the cell suspension in an equivalent amount for each tube and centrifuged at 4° C. at 12,000 rpm for 15 minutes. The supernatant liquid was collected and preserved in ice until the time it was used (crude enzyme solution).

L-dopa was adjusted to a concentration of 0.8 mg/ml with the 0.05 M phosphate buffer (pH 6.8). After the addition of 0.25 ml of the L-dopa solution, 0.25 ml of solutions of the compound (I) of the present invention at various concentrations, and 0.5 ml of the crude enzyme solution, the mixture was immediately mixed, followed by incubation at 25° C. for two hours. Then, the absorption at 475 nm was measured.

Inhibitory Activity to Melanogenesis of B16 Melanoma

About $2.0\times10^5$/ampoule B16 melanoma cell strain preserved in a frozen state in liquid nitrogen was dissolved in a water bath at 37° C. and immediately suspended in 10 ml of a culture medium. After centrifugation at 800 rpm for five minutes, the supernatant liquid was discarded and the cells were suspended in 10 ml of a fresh culture medium. The suspension was again centrifuged under the same conditions, the supernatant liquid was discarded, and the cells were again suspended in a fresh culture medium.

About $4.0\times10^5$ cells were seeded in a 75 $cm^2$ flask. The cells were cultured at 37° C. in a 5% $CO_2$ atmosphere for one week while replacing the medium every 2–3 days. The culture medium in which the cells have grown to bring the medium into a subconfluent state was discarded. The surface of the cultured cells was washed with PBS(−), following which the cells were stripped using 0.25% trypsin. A medium containing serum was added to terminate the trypsin reaction. After loosening the cells by pipetting, the cell suspension was transferred to a centrifugal tube. After centrifugation at 800 rpm for five minutes, the supernatant liquid was discarded and the cells were suspended in a fresh culture medium (not containing phenol red). The number of cells was counted using a cytometer.

The cell suspension was diluted with a medium (not containing phenol red) to make the cell concentration $2\times10^5$ cells/ml. The resulting suspension was seeded in a 96-well plate in an amount of 100 μl/well. The cells were incubated at 37° C. in a 5% $CO_2$ atmosphere for one day. Solutions of the compound (I) of the present invention at various concentrations were prepared in a medium (not containing phenol red). The resulting solutions were added to a 96-well plate in an amount of 100 μl/well. The cells were incubated at 37° C. in a 5% $CO_2$ atmosphere for five days and evaluated according to the following method.

(Method of Evaluation)

1. Amount of Extracellular Melanin

The culture medium was transferred to an assay plate in an amount of 150 μl/well while taking care so that foam was not produced to measure $OD_{450}$ using a microplate reader.

2. Amount of Intracellular Melanin

The plate containing the cells was inverted to discard the remaining culture medium. 0.1 N NaOH-0.1% Triton X-100 was added in an amount of 150 μl/well to dissolve the cells by pipetting. The culture medium was transferred to an assay plate in an amount of 100 μl/well to measure $OD_{450}$ using a microplate reader.

3. Amount of Proteins

Distilled water was added to the assay plate in an amount of 156 μl/well. Then, 4 μl/well of the cell solution remaining after measuring the amount of intracellular melanin was added. Next, 40 μl/well of a Bio-rad protein assay die solution was added, followed by shaking for two minutes. After allowing to stand for five minutes, $OD_{590}$ was measured using a microplate reader.

The results are summarized in Table 4. The compound (I) of the present invention was proven to possess excellent tyrosinase inhibitory activity and melanogenesis inhibitory action. Moreover, in the concentration in which these whitening actions were clearly exhibited, there were no morphological changes in the cells observed by microscopic inspection, nor were there any effects on the number of grown cells and the amount of proteins in the cells recognized.

TABLE 4

Tyrosinase inhibitory activity and melanogenesis inhibitory effect of compound (I) of present invention

|  | IC50 (ng/ml) |
| --- | --- |
| Mushroom tyrosinase | 1.9 |
| B16 tyrosinase | 0.54 |
| B-16/2D2 cells |  |
| Intracellular melanogenesis | 74 |
| Extracellular melanogenesis | 52 |
| Protein synthesis | 900 |

Example 3

The whitening effect of the compound (I) of the present invention was measured according to the following method.

20 subjects were exposed to sunlight for four hours from 11:00 a.m. to 1:00 p.m. over two days in summer. Five days after the exposure to sunlight, a water phase and an alcohol phase having compositions respectively shown in FIG. 5 and FIG. 6 were mixed and dissolved, and the solution was applied to the skin on the medial side of the upper arm of each exposed subject once for every morning and evening over four weeks.

TABLE 5

(Alcohol phase)

| Components | (wt %) |
| --- | --- |
| Ethanol | 55.0 |
| Polyoxyethylene hydrogenated castor oil | 2.0 |
| Antioxidant/antiseptic agent | Appropriate amount |
| Perfume | Appropriate amount |
| Test agent | 0.3–0.1 |

TABLE 6

(Water phase)

| Components | (wt %) |
| --- | --- |
| Glycerol | 5.0 |
| Sodium hexamethacrylate | Appropriate amount |
| Purified water | Remaining part |

After four weeks, the whitening effect was judged for each subject. The effect was judged according to the following standards.

Very good: 80% or more of subjects exhibited a complete response or partial response.

Good: 50–80% of subjects exhibited a complete response or partial response.

Fair: 30–50% of subjects exhibited a complete response or partial response.

Bad: Less than 30% of subjects exhibited a complete response or partial response.

The results are shown in Table 7.

TABLE 7

| Type of test agent | Amount (wt %) | Effect |
| --- | --- | --- |
| Control (no agent added) | — | Bad |
| Kojic acid | 1.0 | Fair |
| Hydroquinone | 1.0 | Good |
| Compound (I) of present invention | 0.3 | Good |
| Compound (I) of present invention | 0.1 | Good |

As shown in Table 7, the compositions containing the compound (I) of the present invention exhibited a melanin pigmentation preventive effect equivalent to or more excellent than the agents used as controls at a smaller dose. In addition, neither abnormalities of the skin, such as erythema or edema, nor any side effects suspected to be caused by the compound of the present invention were seen in the subjects to whom the compound of the present invention was administered.

Example 4

A milky lotion containing the compound (I) of the present invention was prepared by mixing the three components shown in Tables 8, 9, and 10.

TABLE 8

| Components A | (wt %) |
| --- | --- |
| Sucrose fatty acid ester | 1.0 |
| Concentrated glycerol | 6.0 |
| Antiseptic agent (p-hydroxybenzoate) | Appropriate amount |
| Carboxyvinyl polymer | 0.06 |
| Potassium hydroxide | 0.028 |
| Purified water | Remaining part |

TABLE 9

| Components B | (wt %) |
| --- | --- |
| Olive oil | 4.0 |
| Jojoba oil | 4.0 |
| Myristyl lactate | 2.0 |
| Self-emulsifying glycerol monostearate | 1.5 |
| Lipophilic glycerol monostearate | 1.5 |

TABLE 10

| Components C | (wt %) |
| --- | --- |
| Compound (I) of present invention | 0.2 |
| Perfume | 0.2 |

The components A were dissolved by heating and maintained at 80° C. The components B separately dissolved by heating to 80° C. were added to the components A and the components were sufficiently mixed. The mixture was cooled while stirring and the components C were added at 50° C. to obtain a milky lotion.

Example 5

A face lotion containing the compound (I) of the present invention was prepared using the composition as shown in Table 11.

TABLE 11

| Components | (wt %) |
| --- | --- |
| Concentrated glycerol | 4.0 |
| Sorbitol solution (70 wt % aqueous solution) | 4.0 |
| Sodium citrate | 0.3 |
| Polyoxyethylene hydrogenated castor oil | 0.5 |
| Ethanol | 15.0 |
| Compound (I) of present invention | 0.2 |
| Perfume | 0.05 |
| Purified water | Remaining part |

All the components were mixed with stirring at room temperature to obtain a homogeneous solution. The pH of the solution was adjusted to 5.5 to obtain a face lotion.

Example 6

A cream containing the compound (I) of the present invention was prepared using the composition as shown in Table 12.

TABLE 12

| Components | (wt %) |
| --- | --- |
| Stearic acid | 2.0 |
| Stearyl alcohol | 7.0 |
| Hydrogenated lanolin | 2.0 |
| Squalen | 5.0 |
| 2-Octyldodecyl alcohol | 6.0 |
| Polyoxyethylene (25 mol) cetyl alcohol ester | 3.0 |
| Glycerol monostearate | 2.0 |
| Propylene glycol | 5.0 |
| Compound (I) of present invention | 0.2 |
| Sodium hydrogen sulfite | 0.03 |
| Ethylparaben | 0.3 |

TABLE 12-continued

| Components | (wt %) |
| --- | --- |
| Perfume | Appropriate amount |
| Purified water | Remaining part |

Propylene glycol was added to purified water. The mixture was heated and maintained at 70° C. (water phase). The other components were mixed, dissolved by heating, and maintained at 70° C. (oil phase). The oil phase was added to the aqueous phase and preliminarily emulsified. The pre-emulsion was homogeneously emulsified in a homogenizer to obtain a cream.

All agents for external skin application obtained in Examples 4–6 were confirmed to have an effect in the whitening effect examination.

INDUSTRIAL APPLICABILITY

A novel microorganism which produces (E)-4-(2-isocyanovinyl)phenyl α-L-rhamnopyranoside exhibiting an excellent melanogenesis inhibitory action is provided by the present invention. The (E)-4-(2-isocyanovinyl)phenyl α-L-rhamnopyranoside produced by this strain (including mutants) is effective for lightening or whitening pigmentation, spots, freckles, chloasma, and the like after exposure to sunlight and is expected to become a component for a safe and excellent whitening agent.

The invention claimed is:

1. (E)-4-(2-isocyanovinyl)phenyl a-L-rhamnopyranoside or its salt.

2. An agent for external skin application comprising (E)-4-(2-isocyanovinyl)phenyl α-L-rhamnopyranoside or its salt, and an optional component used for common cosmetic compositions, quasi-drugs or medical supplies.

3. The agent according to claim 2, wherein the optional component is an oleum, humectant, thickener, antiseptic agent, emulsifying agent, pigment, powder, pH adjusting agent, medicinal ingredient, UV absorber, antioxidant or perfume.

4. The agent according to claim 2, wherein the agent is in the form of a cream, milky lotion, face lotion, foundation, pack, lotion, gel, solution, or stick.

5. The agent according to claim 3, wherein the agent is in the form of a cream, milky lotion, face lotion, foundation, pack, lotion, gel, solution, or stick.

* * * * *

UNITED STATES PATENT AND TRADEMARK OFFICE
CERTIFICATE OF CORRECTION

PATENT NO. : 7,115,721 B2
APPLICATION NO. : 10/502949
DATED : October 3, 2006
INVENTOR(S) : Akira Nakagawa et al.

It is certified that error appears in the above-identified patent and that said Letters Patent is hereby corrected as shown below:

On the title page, item (73), in the Assignee, "Ltd,, Osaka" should read --Ltd., Osaka--.

Signed and Sealed this

Second Day of January, 2007

JON W. DUDAS
*Director of the United States Patent and Trademark Office*